United States Patent [19]

Phare

[11] Patent Number: 5,397,994
[45] Date of Patent: Mar. 14, 1995

[54] MOISTURE MEASUREMENT GAUGE FOR PARTICULATES INCLUDING A TRANSMISSION LINE FORMING PART OF A RESONANT CIRCUIT

[75] Inventor: Robert W. Phare, Hilliard, Ohio
[73] Assignee: Alkon Corporation, Columbus, Ohio
[21] Appl. No.: 174,206
[22] Filed: Dec. 28, 1993
[51] Int. Cl.6 .................... G01R 27/26; H01P 7/04
[52] U.S. Cl. .................. 324/668; 324/664; 324/675; 324/690; 333/24 C; 333/245
[58] Field of Search ............... 324/652, 663, 664, 667, 324/668, 674, 675, 681, 682, 686, 687, 689, 690, 633, 634, 754; 340/604; 73/73, 74; 333/24 C, 222, 223, 245

[56] References Cited

U.S. PATENT DOCUMENTS

| | | | |
|---|---|---|---|
| 1,822,604 | 9/1931 | Simons et al. | 324/668 X |
| 2,720,624 | 10/1955 | Gunst et al. | 324/668 |
| 2,904,751 | 9/1959 | Parsons | 324/675 X |
| 3,046,479 | 7/1962 | Mead et al. | 324/668 |
| 3,125,717 | 3/1964 | Ghose | 324/332 |
| 3,252,086 | 5/1966 | Lundstrom | 324/668 |
| 3,660,754 | 5/1972 | Tsao et al. | 324/333 |
| 3,684,952 | 8/1972 | Lundstrom | 324/675 X |
| 4,506,241 | 3/1985 | Makimoto et al. | 333/222 |
| 4,560,923 | 12/1985 | Hanson | 324/668 |
| 4,605,914 | 8/1986 | Harman | 333/237 |
| 4,909,070 | 3/1990 | Smith | 324/663 X |
| 5,023,560 | 6/1991 | Gallagher | 324/690 X |

Primary Examiner—Gerard R. Strecker
Assistant Examiner—Diep Do
Attorney, Agent, or Firm—Frank H. Foster

[57] ABSTRACT

A particulate moisture measurement gauge of the type using a resonant electric circuit connected to a diode detector and to an AC signal generator having a frequency near the resonant frequency of the resonant circuit and in which the resonant circuit is electrically coupled to the particulate by a capacitor having the particulate as its dielectric. A probe is formed as a transmission line having a length which is approximately an integral number of one quarter wave lengths long. One end of the transmission line is connected to the circuitry and its opposite, moisture sensing end is immersed in the particulate. Preferably the probe is a rigid, conductive tube with a central rod having a ceramic insulator sealing its moisture sensing end and the circuitry housed in its opposite end.

14 Claims, 5 Drawing Sheets

MOISTURE MEASUREMENT GAUGE FOR PARTICULATES INCLUDING A TRANSMISSION LINE FORMING PART OF A RESONANT CIRCUIT

TECHNICAL FIELD

This invention relates generally to electrical systems for measuring the moisture content of a particulate material, and more particularly relates to the measurement of the moisture content in a flowing, fine aggregate, such as the sand used for mixing portland cement concrete, by means of an electronic apparatus which includes a tuned or resonant circuit.

BACKGROUND ART

Moisture content of many particulate materials is an important parameter for processing or storing the particulate material. The water content of aggregate materials, particularly fine aggregates or sand, is an important parameter in the production of concrete because it is critical to concrete strength. Concrete sand is normally 3% to 10% water and the water content must be measured to determine how much sand and additional water to add to make good quality concrete. Uncontrolled variations in the moisture content of the aggregates is a major problem affecting the production of high specification concrete because relatively small changes in sand moisture have a significant effect upon the workability of the concrete in its plastic state and upon the compressive strength of the cured concrete.

The prior art discloses a variety of systems for gauging the moisture content of particulate materials. These systems include the use of infrared techniques, the detection of neutron backscatter and the measurement of electrical conductivity. Many devices utilize a parallel resonant, electronic circuit which includes a capacitor formed by spaced capacitor plates. A sample of the particulate material is interposed between the capacitor plates. Because the dielectric constant of the particulate is approximately proportional to its moisture content, capacitance changes can be used to detect moisture. To detect capacitance, an AC signal is applied to the resonant circuit, which includes the capacitor having the interposed particulate as a dielectric. The applied AC signal has a frequency near the resonant frequency of the resonant circuit. Because the impedance across a resonant circuit is reduced when the capacitance changes, voltage measurements across the tuned circuit are approximately inversely proportional to moisture content when the resonant circuit is connected in a voltage divider circuit.

In the earliest form of this concept practiced in the prior art, a sample of the material being tested was positioned between the capacitor plates. This concept is illustrated, for example, in U.S. Pat. No. 1,822,604, which illustrates a pair of parallel, planar, capacitor plates. This concept is extended to cylindrical embodiments in which the material being tested was placed within or flowed through an outer cylindrical capacitor plate, with the second capacitor plate formed as a smaller coaxial rod within the pipe. Such structures are illustrated by U.S. Pat. Nos. 2,720,624; 2,904,751; and 3,684,952. These systems provide acceptable performance for those materials for which flow through a pipe is practical.

However, for some materials, such as sand utilized in mixing concrete, flow through a pipe is impractical because of their flow characteristics, their abrasive nature and the large quantity of such materials which are used. The use of batch testing of small samples is also impractical for some applications because of the difficulty of obtaining and measuring representative samples and the inconvenience of repeatedly filling and emptying the testing device.

The prior art further developed the above capacitor testing system by forming the capacitor in a generally planar configuration so that the two capacitor plates are located in the same plane, such as on the wall of a container, but are spaced from each other. As a consequence, an electric field having semi-circular and semi-elliptical electric field lines project from one side of the planar capacitor through the particulate material. Illustrative of that technique are U.S. Pat. Nos. 3,046,479; 3,252,086; and 4,560,923.

The use of the planar capacitor system avoids the need for the batch testing of samples or the need to flow the material through a pipe. That system can give acceptable results where the particulate material has a moisture content which is homogeneously distributed throughout its container, so that the moisture content measured at the container wall where the capacitor plates are positioned in their planar configuration is the same as the moisture content elsewhere.

However, the modern, ready-mix concrete industry uses automated, batch processing equipment. In the modern automated system, the sand is retained in a storage bin and is dispensed from the bin through a controlled feed gate at the bottom of the bin. Automatic control systems weigh the material as it is fed and use the weight information to control the feed gate. The control system also measures the moisture content of the sand and determines the quantity of other materials, including water, to add to the mix.

In an automated system, the sand flows principally through the central portion of the bin and feed gate at high flow rates on the order of 1,000–1,500 pounds per second. The sand located adjacent the walls of the bin may remain relatively static and thus does not have a moisture content which is necessarily representative of the moisture content of the sand actually being dispensed. This eliminates the opportunity to use the planar capacitor configurations of the prior art because they would detect the moisture in the static boundary layer of sand rather than in the sand being dispensed. Furthermore, an attempt to use parallel planar or coaxial capacitor plates between which flow of the sand could be effected is also impractical because of the likely obstruction of the sand flow, the damage and wear upon such capacitor plates, and the likelihood that the plates would cause localized regions of static interrupted flow and voids, causing erroneous readings much like measurements made at the walls of the bin.

It is therefore an object and feature of the present invention to provide an improved moisture measurement gauge which will measure the moisture content of the particulate material in the region where the material actually being utilized is flowing and to do so in a manner which does not impede the flow or create immobilized accumulations of particulate material or voids in the vicinity of the particulate being measured which would cause inaccurate measurements.

It is another Object and feature of the present invention to provide a simple, low cost moisture measurement gauge having improved sensitivity and which eliminates the lossy electrical resistance, cost and mechanical instabilities associated with a lumped inductor.

Another object and feature of the present invention is to provide a moisture detection gauge which is rugged and durable and permits the delicate electronic circuit to be positioned remotely from the moisture sensing elements where the circuitry is both better protected and more easily serviced.

Another object and feature of the present invention is to provide a moisture sensing probe which inherently performs an impedance transformation so that the effective impedance of the tuned circuit is directly proportional to, rather than inversely proportional to, the sand moisture content in order to enhance the simplicity of the detection and display circuitry.

BRIEF DISCLOSURE OF INVENTION

The invention is an improvement upon moisture gauges of the type in which a resonant circuit is connected to both a detector circuit and an AC signal generator having a frequency near the resonant frequency of the resonant circuit, and in which the resonant circuit is electrically coupled to a particulate material for changing the impedance of the resonant circuit in response to the dielectric properties of the material. The improvement is a probe which includes a transmission line connected at its first end to the detector circuit and the signal generator and forming a part of the tuned circuit. The probe has its opposite, moisture sensing, second end spaced from the first end where it can be positioned within the flow of particulate material without significantly impeding or altering that flow. Preferably the probe is a rigid, conductive tube with a central co-axial conductor within the tube and a rigid insulator between the tube and the central conductor for sealing its moisture sensing end.

Figure 1:
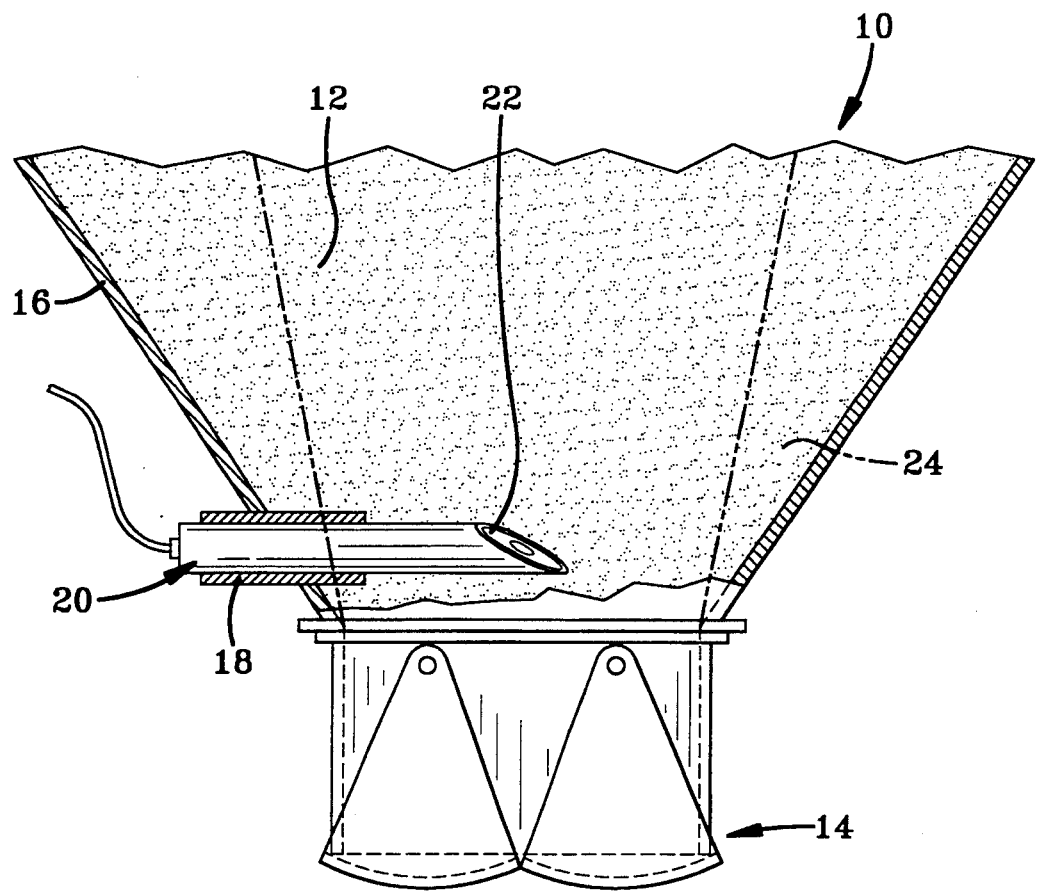
FIG. 1 is a view in vertical section of a sand storage bin and feed gate arrangement in which a preferred embodiment of the invention is mounted.

In describing the preferred embodiment of the invention which is illustrated in the drawings, specific terminology will be resorted to for the sake of clarity. However, it is not intended that the invention be limited to the specific terms so selected and it is to be understood that each specific term includes all technical equivalents which operate in a similar manner to accomplish a similar purpose. For example, the word connected or terms similar thereto are often used. They are not limited to direct connection but include connection through other circuit elements where such connection is recognized as being equivalent by those skilled in the art.

DETAILED DESCRIPTION

FIG. 1 illustrates a conventional sand storage bin 10 containing sand 12 supported above a conventional clam shell feedgate 14. The conical sidewall 16 of the bin 10 is provided with a radially oriented, cylindrical support sleeve 18 welded in a mating aperture through the sidewall 16. A cylindrical moisture measurement probe 20 is supported in the sleeve 18 with its moisture sensing end 22 positioned centrally near the bottom of the bin 10 so that it is located within the flowing stream of the mass of particulate material 12 as it flow downwardly out through the feedgate 14. In this manner, the moisture sensing end 22 measures the moisture in the flowing material being processed where the measurements are not influenced by the relatively static particulate material located in a generally conical envelope 24 outlined in phantom as a boundary layer upon the conical sidewall 16 of the bin 10.

Figure 2:
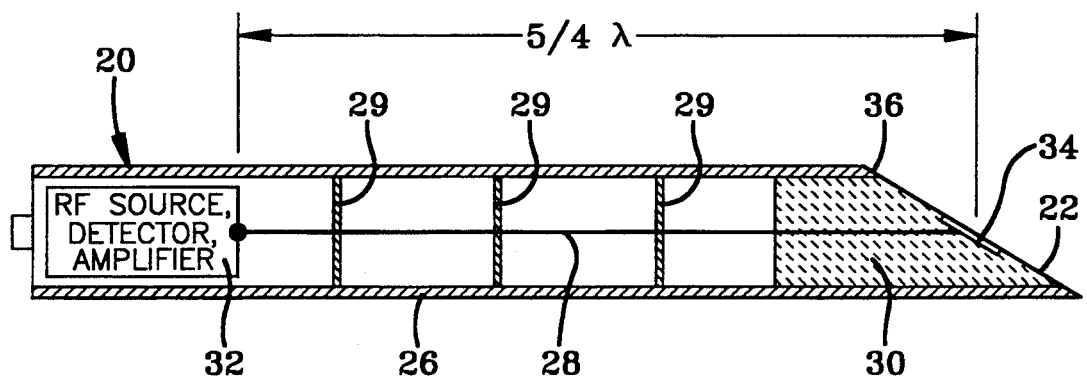
FIG. 2 is a view in axial section through the probe illustrated in FIG. 1.

The probe 20 is illustrated in more detail in FIG. 2. The probe 20 is preferably itself a transmission line formed by a rigid, stainless steel, conductive tube 26 surrounding a central conductor 28, aligned coaxially within the tube 26. The transmission line could alternatively be a conventional transmission line supported by cooperating mechanical support structure. The electronic circuitry 32 connected to the transmission line is conveniently located within the tube 26 and is connected at the first end of the effective, electrical transmission line between the ends of the dimension line in FIG. 2 showing the electrical length to be five quarter wavelengths. The circuitry 32 includes a signal generator and a detector circuit connected to the transmission line and described below. The second, moisture sensing end 22 of the transmission line is physically sealed by a ceramic material 30 forming a rigid insulator to prevent the entry of the particulate material or water and physically support the central conductor 28. The ceramic material 30 accomplishes the physical sealing while leaving the second end of the transmission line sufficiently open circuited or unterminated to permit a fringe field to exist in the particulate material beyond the second end 22. The central conductor 28 is also supported by insulative spacers 29 to retain the central conductor 28 in its axial position and to prevent it from vibrating.

Preferably, the end 36 of the tube 26 at the second, moisture sensing end 22 has its end surface coplanar with the ceramic 30 and oblique with the axis along the central conductor 28 of the transmission line. A central circular disk 34 is advantageously coaxially mounted in the ceramic 30 and electrically Connected to the central conductor 28. This structure forms a capacitor at the end of the transmission line as an integral unitary portion of the transmission line between the central disk 34 and the surrounding peripheral end 36 of the conductive tube 26. The provision of the oblique moisture sensing end 22 permits the probe to be mounted not only with the moisture sensing end 22 centrally positioned within the flowing stream of particulate material, but also permits the moisture sensing end to be oriented obliquely to the vertical flow path. The oblique orientation of the moisture sensing end 22 permits the particulate material to continue to flow in a substantially laminar manner without causing either static flow regions in which particulate matter accumulates, or causing voids or open spaces in the flowing stream of particulate material in the region of the moisture sensing end 22. Preferably, the moisture sensing second end 22 is oriented at an angle of approximately 30° to the central conductor 28. The preferred tube 26 has a diameter of three inches, a total length of 23½ inches, and a transmission line length of 17½ inches between the opposite ends of the central conductor 28. The 17½ inch physical length corresponds to an electrical length in air of 21 inches. The preferred central conductor 28 is a one-eighth inch diameter copper rod. The ceramic 30, or another material, could fill the entire length of the tube 26, but would add both unnecessary cost and weight.

Figure 3:
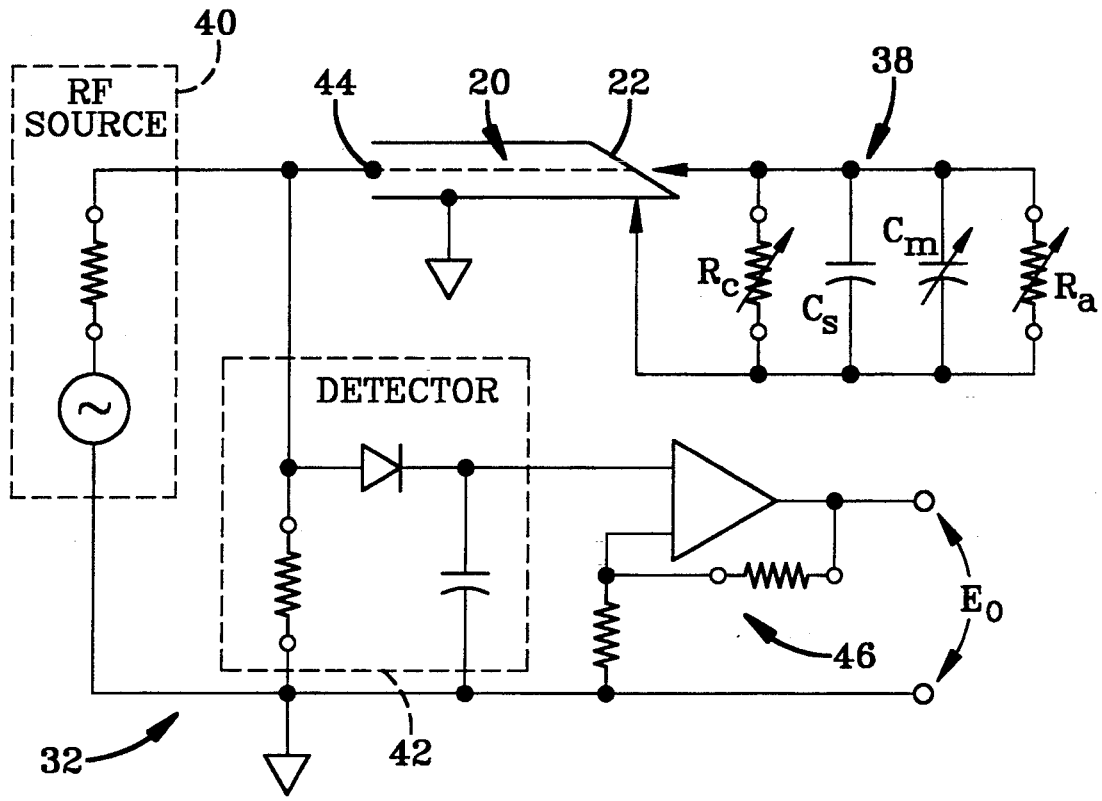
FIG. 3 is a simplified circuit diagram illustrating the principles of operation of the invention.

FIG. 3 schematically and diagrammatically illustrates the electronic circuitry 32 of the present invention, including the probe 20 and a lumped parameter equivalent circuit 38 representing the electrical parameters of the moist particulate material. The electronic circuitry includes an AC signal generator 40 providing an RF source, preferably at 700 MHz and a conventional diode detector 42. The tube 26 is designed to have an effective, electronic length equal to an integral number of ¼ wavelengths. Consequently, the input first end of the probe 20 presents a tuned resonant circuit to the output of the RF source 40. The output voltage of the detector 42 is directly proportional to the peak amplitude of the voltage at the input 44 to the probe 20, which in turn is directly proportional to the input impedance of the probe 20 at its input 44. Therefore, the output signal $E_0$ at the output of a buffer circuit 46 is directly proportional to the input impedance to the transmission line probe 20.

The opposite second end 22 of the probe 20 is immersed in the particulate material approximated by the equivalent circuit 38, which has four parallel circuit elements. The dry sand itself has a dielectric constant of approximately 3 to 5. The component of effective capacitance resulting from the presence of dry sand between the disk 34 at the end of the central conductor 28 and the elliptical end rim 36 at the moisture sensing end 22 is $C_s$. $C_s$ has been experimentally found to be approximately 0.2 picofarads. The presence of moisture increases the dielectric constant of the particulate material so the component of capacitance resulting from the moisture dielectric may be represented as the capacitance $C_m$. The capacitance $C_m$ varies in value, approximately linearly with the moisture content. The moisture based dielectric constant has been experimentally found to be approximately 80. The equivalent resistor $R_c$ represents conductive resistance through the moisture and the resulting energy losses by conduction. The equivalent resistor $R_a$ represents energy loss resulting from dielectric heating of the moisture.

The frequency of operation is chosen with a view to the equivalent circuit 38. The frequency should be chosen so that the reactances of capacitances $C_s$ and $C_m$ at the operating frequency are sufficiently low at the operating frequency that the resistance of equivalent resistor $R_c$ is large enough to be relatively negligible. However, the frequency is also chosen so that it is sufficiently low that the dielectric loss does not become substantial and therefore the resistance of equivalent resistor $R_a$ remains sufficiently large that it too can be considered negligible. Therefore, the equivalent circuit effectively becomes the parallel combination of the constant capacitance $C_s$ and the capacitance $C_m$ which varies in direct proportion to the moisture content.

A length of transmission line which is an odd multiple of one-quarter wavelength forms a resonant circuit. That resonant circuit appears as a series LC resonant circuit at the first end of the transmission line if the second end of the transmission line is open. The preferred embodiment presents such a series LC resonant circuit to the AC signal generator and diode detector because the capacitance at the second end of the transmission line is small and therefore does not depart greatly, from an open circuit. A series resonant circuit presents a low impedance at the resonant frequency and consequently can be illustrated graphically as shown in FIG. 4.

Figure 4:
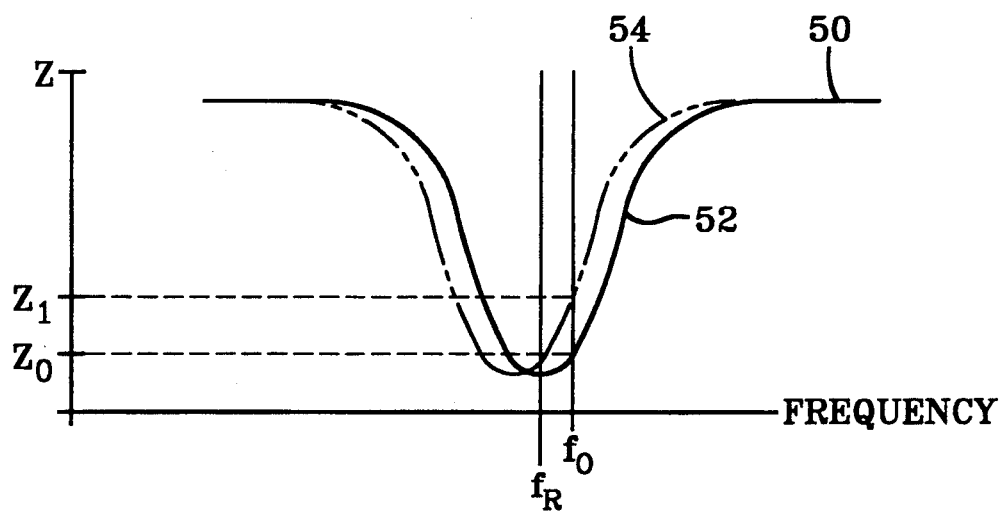
FIGS. 4 and 5 are graphs illustrating the operation of the preferred embodiment of the invention.

FIG. 4 shows, as a solid line 50, a conventional series, resonance peak for a transmission line which is resonant in air at the frequency $f_R$. The resonant peak has a relatively linear portion between each upper and lower knee of the curve. In order to obtain linear operation of the circuit, the operating frequency $f_0$ is preferably chosen as the frequency which is above the resonant frequency and at the lower frequency end of the upper frequency linear portion 52 when the probe is positioned in air.

When the probe is immersed in the sand, or other particulate material, the capacitance at the moisture sensing end 22 of the probe 20 is increased, which detunes the resonance peak of curve 50 from resonance at frequency $f_R$ to another resonant frequency. In this manner, the resonant peak is effectively shifted laterally to a lower frequency, such as, for example, to the resonance peak shown in dashed lines 54. As a result, the impedance across the tuned circuit at the operating frequency $f_0$, seen at the first end of the transmission line, increases from $Z_0$ to, for example, $Z_1$. The distance of the lateral shift of the resonance peak is proportional to the change in capacitance at the moisture sensing end 22 of the probe 20, and therefore the increase in impedance is proportional to the increased capacitance. Since the capacitance is approximately proportional to the moisture content and the impedance is proportional to the voltage output signal, the change in the voltage output signal is directly proportional to the moisture content of the particulate material. By selecting an operating frequency which is at the end of the linear region 52 away from which the impedance will change, the maximum possible linear range of measurement across the entire linear region may be utilized.

Figure 5:
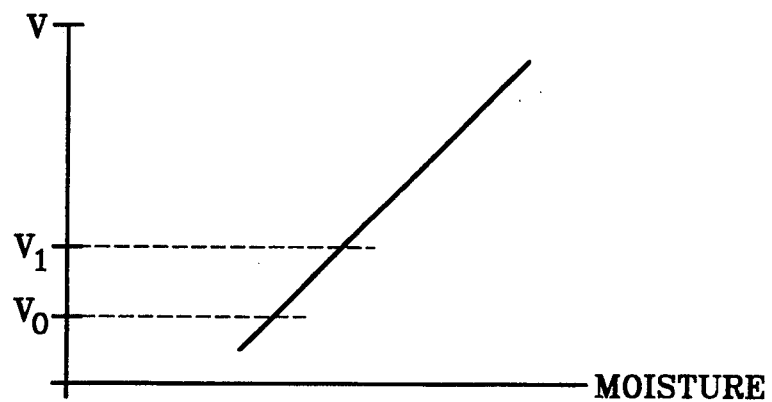

The impedance of a series resonant circuit increases as the operating frequency of a series resonant circuit departs from its resonant frequency. It is desirable that the moisture content being measured be directly proportional to the impedance change, rather than inversely proportional to it in order to simplify the circuit by not requiring an electronic circuit inverter. Therefore, because moisture content is proportional to capacitance and capacitance is proportional to the extent of detuning, the presentation of an apparent series resonant circuit to the AC signal generator and diode detector is preferred because its impedance change as a result of the presence of moisture will be directly proportional to the moisture content. Therefore, the output voltage from the detector is directly proportional to the moisture as graphically illustrated in FIG. 5.

Because the transmission line appears as a parallel resonant circuit at its moisture sensing end 22, the use of a transmission line which has a length of an odd integral multiple of one-quarter wavelength performs an impedance transformation from the apparent parallel resonant circuit at the moisture sensing end 22 to an apparent series resonant circuit at the input 44, to which the electronic circuitry is connected. As illustrated in FIG. 2 for the bin upon which the probe embodying invention has been used, a length of five quarter wavelengths is preferred, but other integral odd multiples of one quarter wavelength may be used for larger and smaller bins.

However, even multiples of the one quarter wavelength may also be used so that an apparent parallel resonant circuit is presented to the AC signal generator and diode detector. This can be accomplished by selecting an operating frequency at the lower frequency side of the lower frequency linear region of parallel resonant peak when such a resonant peak shifts downwardly toward a lower frequency in response to an increase in capacitance at its second, moisture sensing end, the impedance seen at input 49 will similarly vary in direct proportion to the moisture content. Therefore, a variety of various electronic alternatives are available by appropriately designing the length of the transmission line and selecting the operating frequency.

The circuit of FIG. 3 provides an instantaneous measurement of the moisture content of the sand which is present at the moisture sensing end 22. However, the moisture content of the sand varies as sand is travelling through the bin and other sand is added to the bin. For example, sand at the top which is exposed to air may be drier. Sand in different regions of the bin may be at different moisture levels and sand may be added to the bin having a greater or lesser value of moisture. As a result, and as already known in the prior art, the moisture sensing readings can be integrated with respect to time and/or the quantity of sand delivered in order to obtain a total moisture content for a quantity of dispensed sand.

Figure 6:
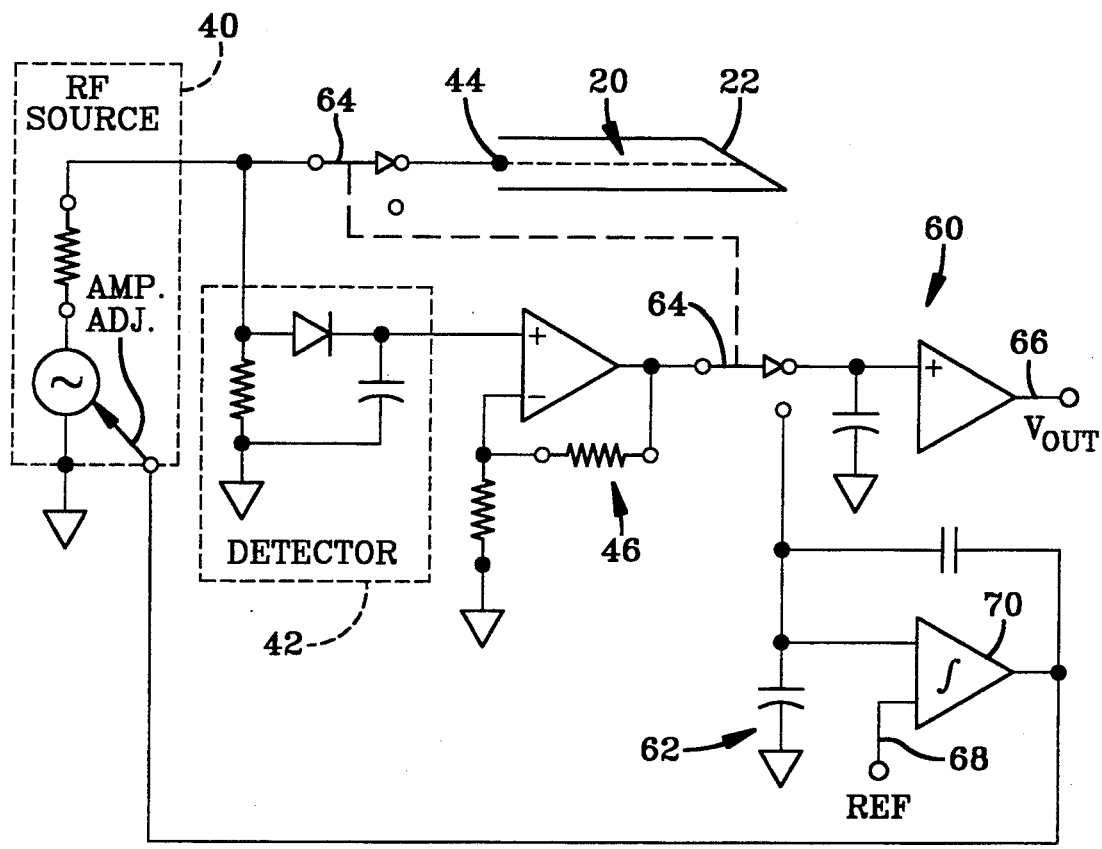
FIG. 6 is a more detailed circuit illustrating additional principles of operation of the preferred embodiment of the invention.
Figure 7:
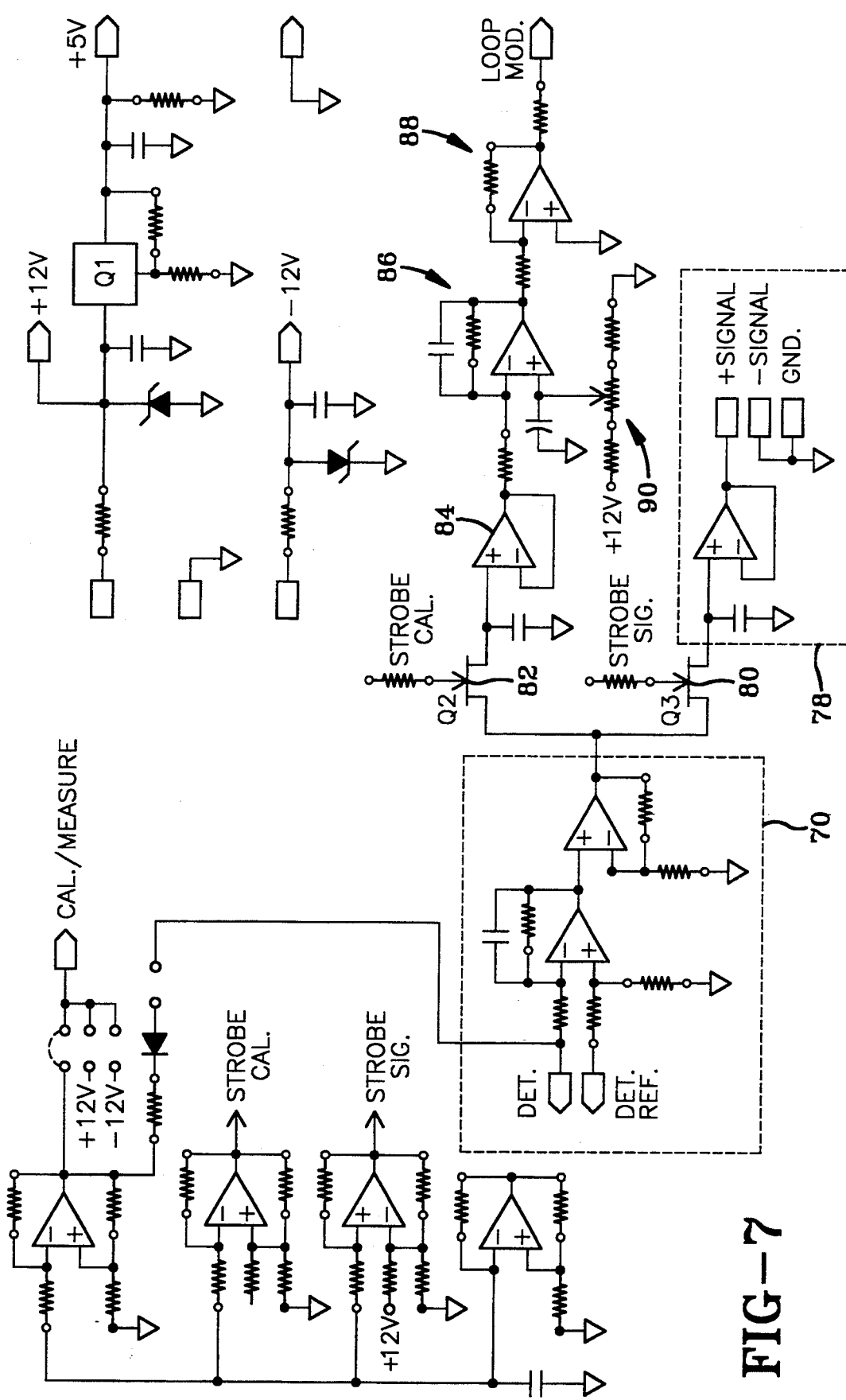
FIGS. 7 and 8 are detailed schematic diagrams of the preferred embodiment of the invention.
Figure 8:
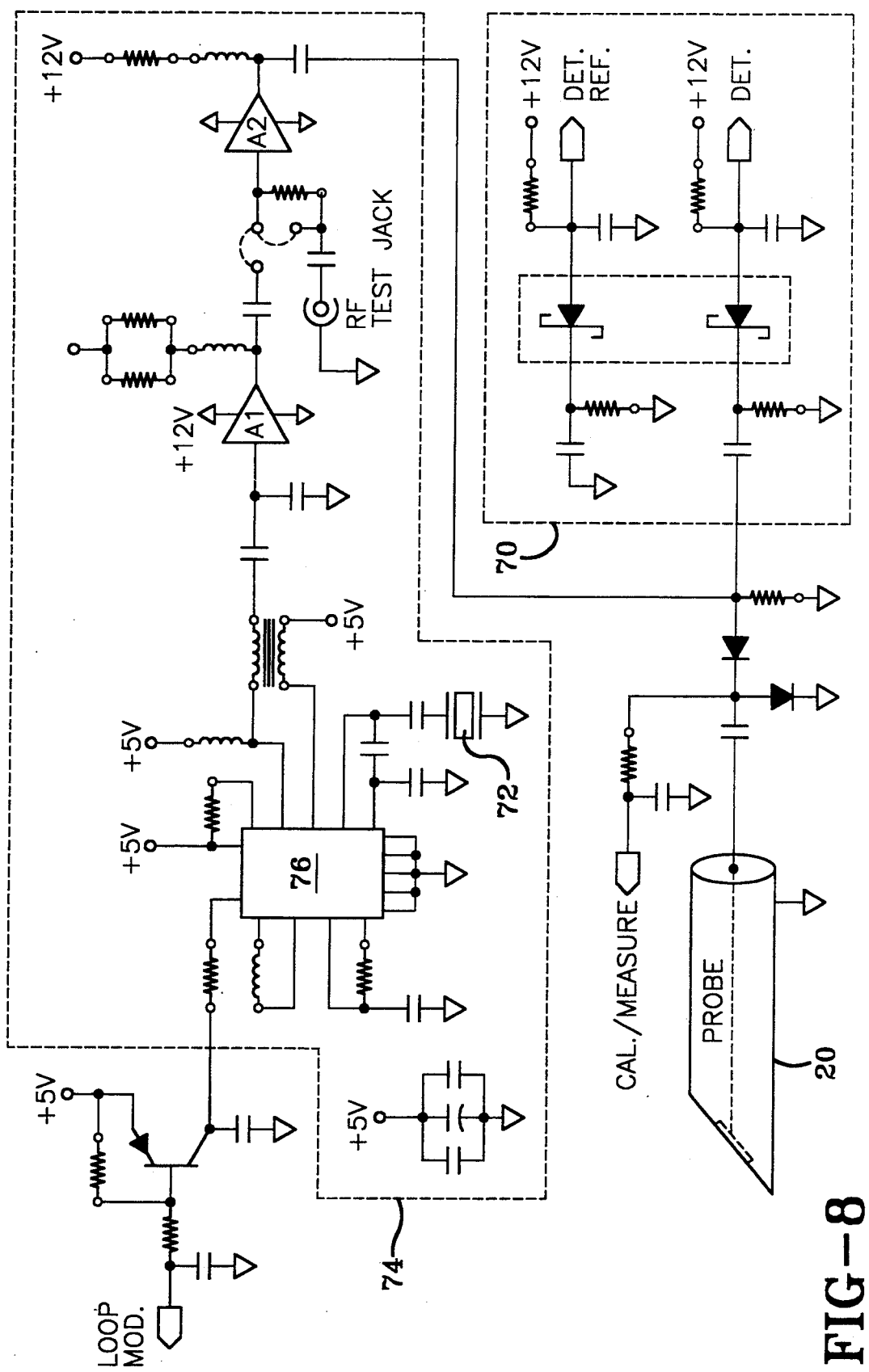

FIGS. 6–8 illustrate additional features of the preferred embodiment which are not unique or inventive with respect to the invention.

FIG. 6 illustrates the use of a sample and hold circuit 60 and an RF signal generator amplitude control circuit 62. A double pole/double throw electronic switch 64 in one position connects the output of the signal generator 40 to the probe, while simultaneously connecting the output of the buffer circuit 46 to the sample on hold circuit 60. In this manner conventional sampling techniques are utilized to obtain an output voltage at output terminal 66, which is proportional to the impedance at the input end 44 of the probe 20 and therefore proportional to moisture.

In the other position of the double pole/double throw switch 64, the RF signal from the signal generator 40 is not connected to the probe, but is connected only to the detector circuit 42. In that second position of the switch 64, the output of the buffer 46 is instead connected to the RF amplitude control circuit 62. A constant reference voltage 68 is connected at one input of operational amplifier 70 and the output of buffer 46 is connected to its other input. The operational amplifier 70 is connected to an input and a feedback capacitor to form an integrator in the conventional manner. Consequently, the op-amp 70 provides an output which is an integration of the difference between the reference level at input 68 and the detected level from the RF source 40. The output of the operational amplifier 70 is connected to the RF source and electronically adjusts the amplitude output of the signal generator 40. Thus, it can be been that the amplitude control circuit provides a negative feedback control loop to maintain a constant output amplitude from the AC signal generator 40 in accordance with conventional feedback control principles.

FIGS. 7 and 8 illustrate the preferred, detailed circuit embodying the invention. It includes the probe 20, connected to the diode detector 70, which uses a conventional biased. Shottky diode detector having two balanced diodes and a differential amplifier so the detector output is not significantly influenced by temperature. The AC signal generator 74 is controlled by crystal 72 and uses a single chip transmitter module 76 designed for personal communications circuitry. The sample and hold circuit 78 is alternately connected to the output of detector 70 by means of electronic switching element 80. Another switching element 82 alternately connects the output of detector 70 to a sample and hold circuit 84 and integrator circuit 86, which also has the reference voltage divider circuit 90 connected to its non-inverting input, and output buffer 88 to perform the control function described in connection with FIG. 6.

Although 700 MHz is the preferred frequency, the invention can also be practiced at other frequencies in the UHF band. The UHF band is that position of the spectrum approximately in the range of 300 MHz to 3000 MHz.

While certain preferred embodiments of the present invention have been disclosed in detail, it is to be understood that various modifications may be adopted without departing from the spirit of the invention or scope of the following claims.

I claim:

1. An improved moisture measurement gauge in which a resonant circuit is connected to a detector circuit and an AC sisal generator having an output signal at a frequency near the resonant frequency of the resonant circuit and in which the resonant circuit is electrically coupled to a particulate material for changing impedance in response to the dielectric properties of the material, wherein the improvement comprises:

a probe including a transmission line connected at a first end to the detector circuit for detecting signal amplitude and to the signal generator generating the signal near the resonant frequency, the transmission line forming at least part of the resonant circuit and having the opposite second end of the transmission line physically sealed to prevent the entry of particulate material and electronically sufficiently open to permit a fringe field to exist beyond the second end.

2. An apparatus in accordance with claim 1 wherein the transmission line has a length approximately equal to an integral multiple of one quarter wavelength.

3. An apparatus in accordance with claim 2 wherein the integral multiple is an odd number.

4. An apparatus in accordance with claim 1 wherein the transmission line is coaxial.

5. An apparatus in accordance with claim 4 wherein the transmission line has a length approximately equal to an integral number of one quarter wavelengths.

6. An apparatus in accordance with claim 5 wherein the transmission line has an outer conductor formed by a rigid conductive tube, a central conductor coaxial with the tube, and a rigid insulator between the conductors.

7. An apparatus in accordance with claim 6 wherein the opposite second end of the transmission tube has an end surface which is oblique with the axis of the transmission line.

8. An apparatus in accordance with claim 7 wherein the probe is mounted to a support near a flow path of the particulate material with the second end of the transmission positioned in the flow path and having said end surface oriented obliquely to the flow path.

9. An apparatus in accordance with claim 6 wherein the detector circuit and the generator are mounted within the tube near the first end of the transmission line.

10. An apparatus in accordance With claim 1 wherein the AC generator frequency is substantially at a frequency above the resonant frequency, near the lower frequency end of the linear portion of the resonant peak when the probe is in air.

11. An apparatus in accordance with claim 1 wherein the AC generator frequency is substantially a UHF band frequency.

12. A method for measuring the moisture content of a mass of particulate material, the method comprising:

(a) applying an AC signal to a first end of a transmission line forming at least part of a resonant circuit, the AC signal having a frequency near the resonant frequency of the resonant circuit;

(b) immersing the second opposite end of the transmission line into the mass of particulate material; and (c) detecting the signal amplitude at said first end.

13. A method in accordance with claim 12 wherein the mass is flowing.

14. A method in accordance with claim 13 further comprising orienting the second end of the transmission line obliquely to the direction of flow.

* * * * *